United States Patent [19]

Dussourd d'Hinterland et al.

[11] 4,314,994
[45] Feb. 9, 1982

[54] PROCESS FOR OBTAINING A PLASMINOGEN ACTIVATOR

[75] Inventors: Lucien Dussourd d'Hinterland; Gerard Normier, both of Castres, France

[73] Assignee: Pierre Fabre S.A., Paris, France

[21] Appl. No.: 172,029

[22] Filed: Jul. 24, 1980

[30] Foreign Application Priority Data

Jul. 27, 1979 [FR] France ................. 79 19432

[51] Int. Cl.³ ............... A61K 35/12; A61K 35/14
[52] U.S. Cl. .................................. 424/95; 424/103; 424/105; 424/101
[58] Field of Search ............ 424/101, 105, 95, 103, 424/94

[56] References Cited

U.S. PATENT DOCUMENTS 3,998,947 12/1976 d'Hinterland ................... 424/94

OTHER PUBLICATIONS

Thorsen et al.–Chem. Abst., vol. 77, (1972), p. 112, 034k.

*Primary Examiner*—Sam Rosen
*Attorney, Agent, or Firm*—Alan H. Levine

[57] ABSTRACT

The present invention relates to an improved process for the preparation of plasminogen activator.

This is a process for separating a plasminogen activator according to U.S. Pat. No. 3,998,947 characterized in that it comprises at least the following stages:

(i) selective adsorption of the said activator on a support with specific affinity comprising soluble fragments of fibrin covalently bonded to an insoluble matrix; and (ii) elution of the activator from the fibrin bearing the adsorbed activator.

The plasminogen activator obtained is useful in the prevention and treatment of thrombosis.

12 Claims, No Drawings

PROCESS FOR OBTAINING A PLASMINOGEN ACTIVATOR

BACKGROUND OF THE INVENTION

The present invention relates to an improved process for the preparation of a plasminogen tissual activator as described in French Pat. No. 73 42981 filed on Dec. 3, 1973 in the name of Pierre Fabre S.A. and in the equivalent patents, U.S. Pat. No. 3,998,937 and British Pat. No. 1,492,959 which are mentioned here as references.

Hereinafter, the terms "plasminogen tissual activator" or "plasminogen activator" essentially designate an activator described in the above-mentioned patents.

The process for the preparation of the said plasminogen tissual activator described in the above-mentioned patents has the disadvantage of necessitating numerous stages of absorption in saline solutions of differing concentration before obtaining a high purity product.

We have devised a new process for the preparation on a large scale of this plasminogen activator making use of the natural affinity of tissual plasminogen activators for fibrin. In effect, fibrin has the property of selectively fixing this plasminogen activator from among other inactive proteins and of thus effecting very rapid separation.

This process has the advantage that it can be carried out on a large scale and thus of producing a plasminogen activator having a specific activity which is substantially better than that of the product forming the subject of the main application.

The direct use of fibrin, such as described by certain authors, presents numerous problems, of which the main ones are that it is not possible to work on a large scale and on the other hand to liberate at the same time only the plasminogen activator, the soluble fragments of fibrin possessing undesirable properties.

The process forming the object of the present invention has the advantage of isolating from fibrin the soluble fragments carrying the fixing site for the plasminogen activator and of fixing these fragments by covalence on an insoluble matrix. The support thus prepared is totally insoluble. It possesses mechanical properties suitable for industrial application and can be reused numerous times without loss of its properties.

Moreover, the said activator can be combined with a sulphated polysaccharide, as described in Certificate of Addition No. 75 13 932 filed on May 5, 1975, and can benefit from the potentiation resulting from this combination.

SUMMARY OF THE INVENTION

The present invention, therefore, relates to an improvement to the process for the preparation of a plasminogen activator according to the above-mentioned patents, characterised in that it comprises at least the following stages:
(i) selective adsorption of the said activator on a support with specific affinity comprising soluble fragments of fibrin fixed by covalence on an insoluble matrix; and
(ii) elution of the activator from the support bearing the adsorbed activator.

In a preferred embodiment of the process according to the present invention, the support with specific affinity is prepared by covalent coupling of soluble fragments isolated from fibrin onto a rigid matrix which can be notably either a dextran polymer activated by cyanogen bromide or a porous glass, such as porous aminated silica.

The soluble fragments of fibrin are preferably fragments soluble in a phosphate buffer of pH 7.4 containing uria, in particular in a concentration of 6 M.

DETAILED DESCRIPTION OF THE INVENTION

One of the significant advantages of the process according to the present invention is that the activator can be eluted by a mere alteration of the pH of the solution placed in contact with the activator+support complex.

Thus, in a preferred embodiment of the process according to the present invention, selective adsorption is carried out starting from an aqueous phase containing the plasminogen activator at a pH of between 6 and 8 by filtration of this solution on the support of specific affinity previously placed in a chromatographie column. The plasminogen activator is retained in these conditions while the inactive proteins are carried away.

Similarly, in a preferred embodiment, the plasminogen activator is eluted from the fibrin by an aqueous solution at a pH of between 3 and 5, preferably with the aid of potassium acetate - acetic acid buffer at a pH of approximately 4.2. This elution is preferably carried out cold at a temperature of between 0° and 10° C., preferably at 4° C. Although other methods of carrying out this process can be considered, it is preferable to treat a clarified solution of plasminogen activator by adding some fibrin to it, the pH of this aqueous solution being buffered to a pH of 7.4 by means of a phosphate buffer. Under these conditions the fibrin bearing the adsorbed plasminogen activator can be separated by precipitation and preferably by centrifugation. Of course, the support bearing the adsorbed plasminogen activator can, if necessary, be washed several times with an aqueous solution, in particular a phosphate buffer at a pH of 7.4, for example cold so as to eliminate all the inactive proteins.

The aqueous phase to be treated can be obtained by various processes, in particular by those described in the above-mentioned patents and, in particular, by:
(a) extraction of crushed animal organs with an aqueous solution at a pH of between 3 and 5;
(b) salting out the solution obtained by addition of a salt; and
(c) absorption of the precipitate obtained by an aqueous solution at a pH of between 7 and 9.

In a preferred embodiment of the process according to the invention, the aqueous phase to be treated is obtained from a pulp of organs crushed and frozen in a potassium acetate - acetic acid buffer at a pH of 4.2. Under these conditions, the untreated extract containing the plasminogen activator in the aqueous phase is obtained and the various residues can be eliminated by passage over a separator and/or by centrifugation.

To complete the beginning of this treatment, the aqueous solution can be treated with some crystalline ammonium sulphate, for example at a concentration of the order of 250 g/l, in order to obtain a precipitate concentrated in plasminogen activator which, after absorption in the phosphate buffer at a pH of 7.4, will constitute the phase to be treated by the stages described above.

Finally, the eluate obtained after separation of the fibrin can be concentrated by any suitable method and, in particular, by dialysis or ultrafiltration against a phosphate buffer or any other medium compatible with later therapeutic use.

Other characteristics of the process according to the present invention can be determined from the Example to be described below.

As described in the above-mentioned patents, the animal organs used are preferably selected from among the lungs, hearts and kidneys of pigs, calves, bullocks, horses, lambs, sheep or the ovaries or uteri of pigs, cattle and sheep. It is particularly preferred to use pigs' ovaries or uteri.

The fibrin used can be prepared, for example, from the blood of animals such as pigs, bullocks, horses or sheep and can be subjected to several preliminary washing treatments with water and with phosphate buffer and then dried. This fibrin is preferably stored at a low temperature in a hermetic wrapping.

EXAMPLE

Some sows' ovaries are removed in an abattoir and are immediately frozen to $-40°$ C. and crushed at this temperature. These crushed frozen organs constitute the raw material used for the preparation of the tissual activator according to the present invention.

300 l of a potassium acetate - acetic acid buffer at a pH of 4.2 are added to 100 kg of crushed and frozen organs and are then extracted for 4 hours at $+4°$ C.

The residue of organs is eliminated by passage in a continuous solid-liquid separator and the supernatant phase is then clarified by continuous centrifugation at 15,000 rpm at $+4°$ C.

The aqueous extract clarified in this way is collected and some crystalline ammonium sulphate is then added to it in a proportion of 250 g/l. After complete dissolution of the ammonium sulphate, the mixture is left cold for about 12 hours in order to allow a precipitate to develop. The untreated precipitate is collected by continuous centrifugation at 15,000 rpm a $+4°$ C. The supernatant is eliminated.

The untreated precipitate containing the activity is absorbed cold by 200 l of phosphate buffer at a pH of 7.4 for 4 hours and the mixture obtained is then clarified by centrifugation at 15,000 rpm.

PREPARATION OF SUPPORT WITH SPECIFIC AFFINITY

Starting with soluble fibrin, 1,000 g of washed and dried fibrin are extracted with 5,000 ml of phosphate buffer, pH 7.4, containing 6 M uria for 2 hours in the cold. The residue is removed by centrifugation and the aqueous fraction containing soluble fragments of fibrin is collected.

The fragments of fibrin carrying the fixation sites for the plasminogen activator are then precipitated from their solution by ammonium sulphate of 60% saturation for 3 hours in the cold.

The precipitate is collected by centrifugation and then redissolved in 5,000 ml of phosphate buffer of pH 7.4 and dialysed against 100 l of the same buffer for 15 hours at $+4°$ C.

The soluble fragments of fibrin are then lyophilised before being coupled by covalence on an insoluble matrix.

Two types of matrix can be used with equal effect:
(a) dextran polymers activated by cyanogen bromide of the type used commercially for this purpose, and
(b) commercial porous glasses to which protein ligands can also be coupled by covalence by means of glutaraldehyde.

(1) USE OF DEXTRAN POLYMERS

The lyophilisate of the fibrin ligand is taken up in 1,000 ml of $NaHCO_3$ coupling buffer, 0.1 M pH 8.3, containing 0.5 M NaCl, and then this solution is mixed for 2 hours at ambient temperature with 150 g of dextran gel activated by CNBr, which has previously been swollen in 30 l of 1 mM HCl and dried.

The gel is collected, dried and then washed with 10 l of coupling buffer.

The free sites remaining on the gel are saturated with a solution of 1 M glycine at pH 8.5.

The washed gel on which the fibrin ligands are fixed constitutes the support with specific affinity. It is introduced as such into a chromatographie column and equilibrated with phosphate buffer of pH 7.4.

(2) USE OF POROUS GLASSES 10 g of porous aminated silica is stirred for one night at ordinary temperature in 2,000 ml of a solution of 5% glutaraldehyde in a phosphate buffer of pH 7.4.

The activated porous glass is then decanted and washed several times with the phosphate buffer of pH 7.4.

The lyophilisate of the fibrin ligand is taken up in 2,000 ml of phosphate buffer of pH 7.4 and stirred for 3 hours at 4° C. with the 10 g of activated porous glass.

The support thus produced is washed with the phosphate buffer of pH 7.4 and the remaining free sites are saturated with a 1 M solution of glycine of pH 8.5.

The support with specific affinity is then washed, introduced into a chromatographie column and equilibrated with phosphate buffer of pH 7.4.

SELECTIVE ADSORPTION OF THE PLASMINOGEN ACTIVATOR

The clarified solution of plasminogen activator in phosphate buffer of pH 7.4 is chromatograhed on the support of specific affinity described above. All the activity is thus retained on the column and the effluent is eliminated.

The column is then washed to eliminate completely the non-fixed inactive proteins. A first washing is carried out with phosphate buffer of pH 7.4 and then a second washing with distilled water until no trace of proteins can be detected in the effluent.

ELUSION OF PLASMINOGEN ACTIVATOR

The activity fixed on the support is eluted by means of a potassium acetate - acetic acid buffer of pH 4.2. The eluate is fractionated and the activity is measured in each fraction.

The fractions containing the plasminogen activator are collected together and concentrated to one-fifth of their volume by ultrafiltration on a membrane with a cut-off at a molecular weight of 10,000 daltons, at low temperature. From 2 to 4 l of concentrate are thus obtained, which are neutralised to pH 7.4 with dilute NaOH and then dialysed for 18 hours against acetate buffer of pH 7.4 in the cold to eliminate acetate ions.

The dialysed solution is then sterilised by filtration over a $0.2\mu$ membrane.

A sample of sterile filtrate is removed to check the protein content by the Lowry method.

The proteins are measured by the method according to Lowry (O. H.), Rosebrough (N. J.), Farr (A. L.) and Randall (R. J.), J. Biol. Chem (1951); and the activity of the solution is then distributed into sterile bottles and lyophilised under sterile conditions.

The activity is determined by the method involving measurement of the lysis time of a standard coagulum, the principle of which is as follows:

A coagulum is formed with some fibrinogen rich in plasminogen and in the presence of the tissual activator which is thus distributed in the mass of the fibrin. The action of the activator on the plasminogen causes the liberation of plasmin which, in turn, destroys the fibrin and causes lysis of the coagulum. The lysis time is proportional to the quantity of activator present and this method is gauged with a standard preparation of urokinase. There is a linear relationship between the lysis time and the activity between 10 minutes and 16 minutes under the operating conditions employed.

The solution obtained is then sealed under sterile conditions and subjected to various checks of sterility, of activity and of innocuousness.

After lyophilisation, the product is stored at $+4°$ C. where it maintains its activity for several months.

Under these conditions, a product containing between $20.10^6$ and $50.10^6$ units per 100 kg of fresh organs is obtained from a product containing between 15,000 and 20,000 units per mg of proteins.

The pharmacological properties of the tissual activator obtained by this process are identical to those described in the above-mentioned Patents.

However, the degree of purification is better and permits a specific activity of beteeen 15,000 and 20,000 units per mg of proteins to be obtained, as stated above.

Moreover, the great affinity for fibrin of the plasminogen activator isolated in this way makes it particularly interesting in the therapeutic field for the treatment of thrombosis.

Thus, the present invention also relates to a plasminogen activator obtained by the process of the present invention and to its use as a drug.

We claim:

1. A process for separating a tissual plasminogen activator, which comprises at least the following steps:
   (i) selectively absorbing said activator on a support with specific affinity comprising soluble fragments of fibrin covalently bonded to an insoluble matrix; and
   (ii) eluting the activator from the fibrin bearing the adsorbed activator.

2. A process according to claim 1, wherein the insoluble matrix is a dextran polymer activated by cyanogen bromide or a porous glass.

3. A process for separating a plasminogen activator according to claim 1, wherein the selective adsorption of the activator is carried out in an aqueous solution at a pH of between 6 and 8.

4. A process for separating a plasminogen activator according to claim 3, wherein the selective adsorption is carried out in an aqueous phase in the presence of a phosphate buffer at a pH of 7.4.

5. A process for separating a plasminogen activator according to claim 1, wherein the activator is eluted by contacting the support bearing the adsorbed activator with an aqueous phase at a pH of between 3 and 5.

6. A process for separating a plasminogen activator according to claim 5, wherein the activator is eluted from the support by contacting the support bearing the adsorbed activator with a potassium acetate - acetic acid buffer at a pH of 4.2.

7. A process for separating a plasminogen activator according to claim 1, wherein separation is carried out cold.

8. In a process for the preparation or separation of a plasminogen activator wherein an extract powder of animal organs are treated in several purifying steps to give a precipitate containing the desired plasminogen activator, the improvement which comprises the selective adsorption of the plasminogen activator through the addition of soluble fragments of fibrin fixed by covalence on an insoluble rigid matrix and the elution of the activator from the fibrin support.

9. In the process of claim 8, the use of either a dextran polymer activated by cyanogen bromide or a porous glass for the rigid matrix.

10. In the process of claim 8, the carrying out of the selective absorption in an aqueous solution at a pH between 6 and 8.

11. In the process of claim 8, eluting the activator by contacting the fibrin support with an aqueous phase at a pH between 3 and 5.

12. In the process of claim 8, wherein the improvement comprises the carrying out of the separation of the plasminogen activator at a temperature between 0° C. and 10° C.

* * * * *